US00PP31864P2

(12) United States Plant Patent
Frick

(10) Patent No.: US PP31,864 P2
(45) Date of Patent: Jun. 16, 2020

(54) ***ACER PALMATUM* TREE NAMED 'MONFRICK'**

(50) Latin Name: ***Acer palmatum* var. *dissectum***
Varietal Denomination: MONFRICK

(71) Applicant: Craig Frick, Chaska, MN (US)

(72) Inventor: Craig Frick, Chaska, MN (US)

( * ) Notice: Subject to any disclaimer, the term of this patent is extended or adjusted under 35 U.S.C. 154(b) by 0 days.

(21) Appl. No.: 16/501,080

(22) Filed: Feb. 19, 2019

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./224

CPC ... A01H 5/00; A01H 5/04; A01H 5/12; A01H 6/00; A01H 5/02; A01H 5/08
See application file for complete search history.

(56) References Cited

PUBLICATIONS

Issuu Monrovia Tool Kit 2018 retrieved on Oct. 31, 2019, retrieved from the Internet at https://issuu.com/monrovia4/docs/monrovia_tool_kit_aug_20_final, cover page p. 41. (Year: 2018).*

* cited by examiner

*Primary Examiner* — June Hwu
(74) *Attorney, Agent, or Firm* — Cassandra Bright

(57) ABSTRACT

A new and distinct *Acer palmatum* var. *dissectum* tree named 'MONFRICK' is disclosed, characterized by unique cold tolerance, observed to tolerate cold temperatures to USDA Zone 4 with minimal tip die back. Plants are dwarf and weeping with deeply dissected foliage. Fall color greyed-red to red. The new variety is a dwarf tree, typically used for outdoor garden or container use.

3 Drawing Sheets

Latin name of the genus and species: *Acer palmatum* var. *dissectum.*

Variety denomination: 'MONFRICK'.

BACKGROUND OF THE INVENTION

The new cultivar is a product of chance discovery. The new variety was discovered as a chance seedling emerging among a planting of various *Acer palmatum* var. *dissectum* trees. The inventor discovered this seedling in June of 2012 at a private garden in Eden Prairie, Minn.

Asexual reproduction of the new cultivar 'MONFRICK' was first performed during 2013 at a commercial nursery in Dayton, Oreg. This was conducted by the conventional commercial practice of grafting semi-softwood cuttings of the new variety onto *Acer palmatum* seedling rootstock. Subsequent propagation has shown that the unique features of this cultivar are stable and have been reproduced true to type for five successive generations. First public access to plants of the variety occurred during March of 2018 in the United States. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'MONFRICK' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONFRICK' grown in Dayton, Oreg. These characteristics in combination distinguish 'MONFRICK' as a new and distinct *Acer palmatum* cultivar:

1. Observed cold hardy to USDA Zone 4 with little or no tip dieback.
2. Weeping habit with an overall rounded shape.
3. Greyed-Red and Red Autumn coloration of the leaf
4. Fine, deeply dissected foliage.

PARENT COMPARISON

The parentage is unknown.

COMMERCIAL COMPARISON

Plants of the new cultivar 'MONFRICK' are similar to plants of *Acer palmatum* var. *dissectum* 'Crimson Queen', unpatented, in most horticultural characteristics, however, plants of the new cultivar 'MONFRICK' differ in the following;

1. The new variety is observed cold hardy to Zone 4, 'Crimson Queen' is observed cold hard to Zone 5.
2. 'Crimson Queen' has narrower, more feathery foliage than the foliage of 'MONFRICK'.

Plants of the new cultivar 'MONFRICK' are similar to plants of the unpatented commercial variety, *Acer palmatum* var. *dissectum* 'Red Dragon' in most horticultural characteristics, however, plants of the new cultivar 'MONFRICK' differ in the following;

1. The new variety is observed cold hardy to Zone 4, 'Red Dragon' is observed cold hard to Zone 5.

2. The new variety is more dwarf in form than 'Red Dragon'.
3. Fall foliage of the new variety has more red tones than the greyed-purple tones of 'Red Dragon'.

BRIEF DESCRIPTION OF THE PHOTOGRAPHS

The accompanying photograph in FIG. 1 illustrates in full color a close up view of typical foliage of 'MONFRICK' grown outdoors, with some Fall coloration to the foliage.

Figure 1:
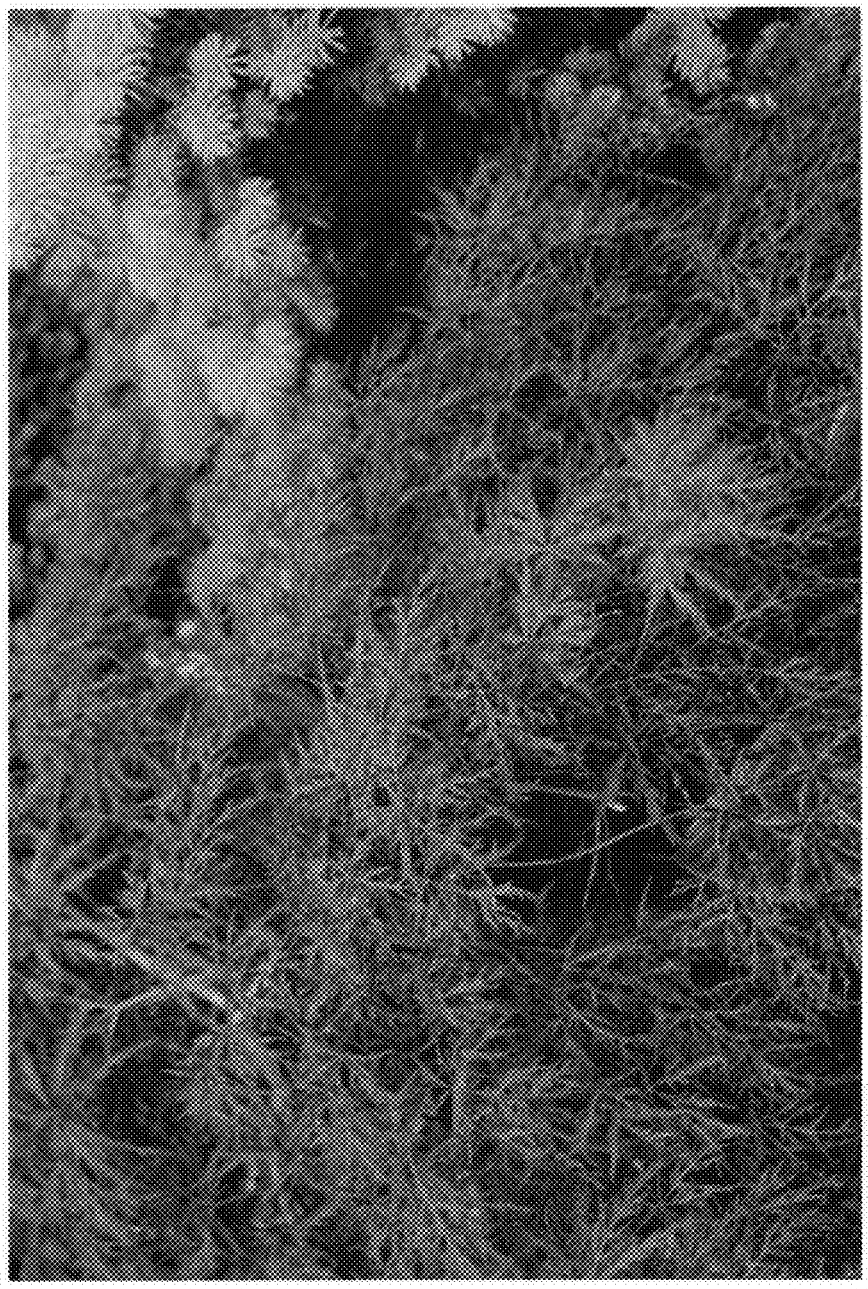
Figure 2:
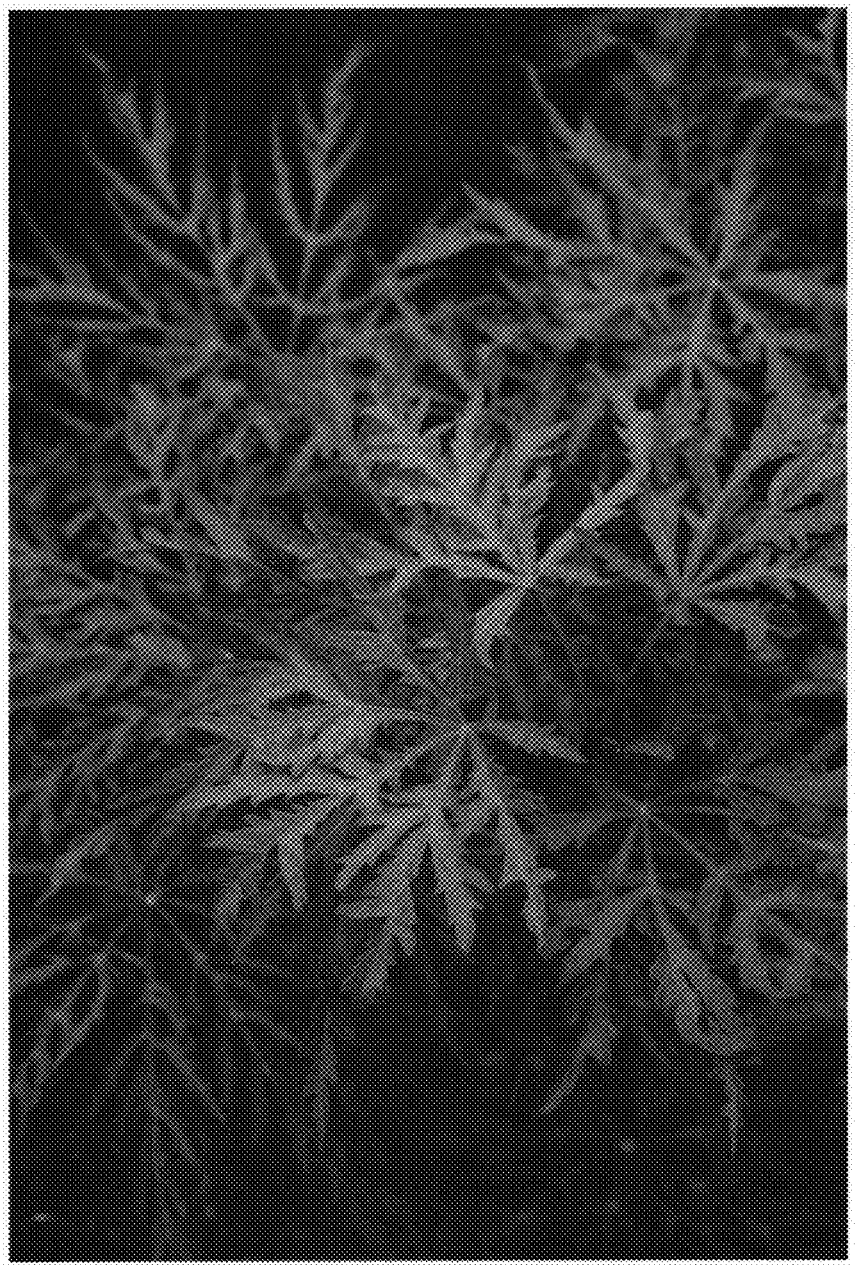
FIG. 2 illustrates the Fall foliage coloration.
Figure 3:
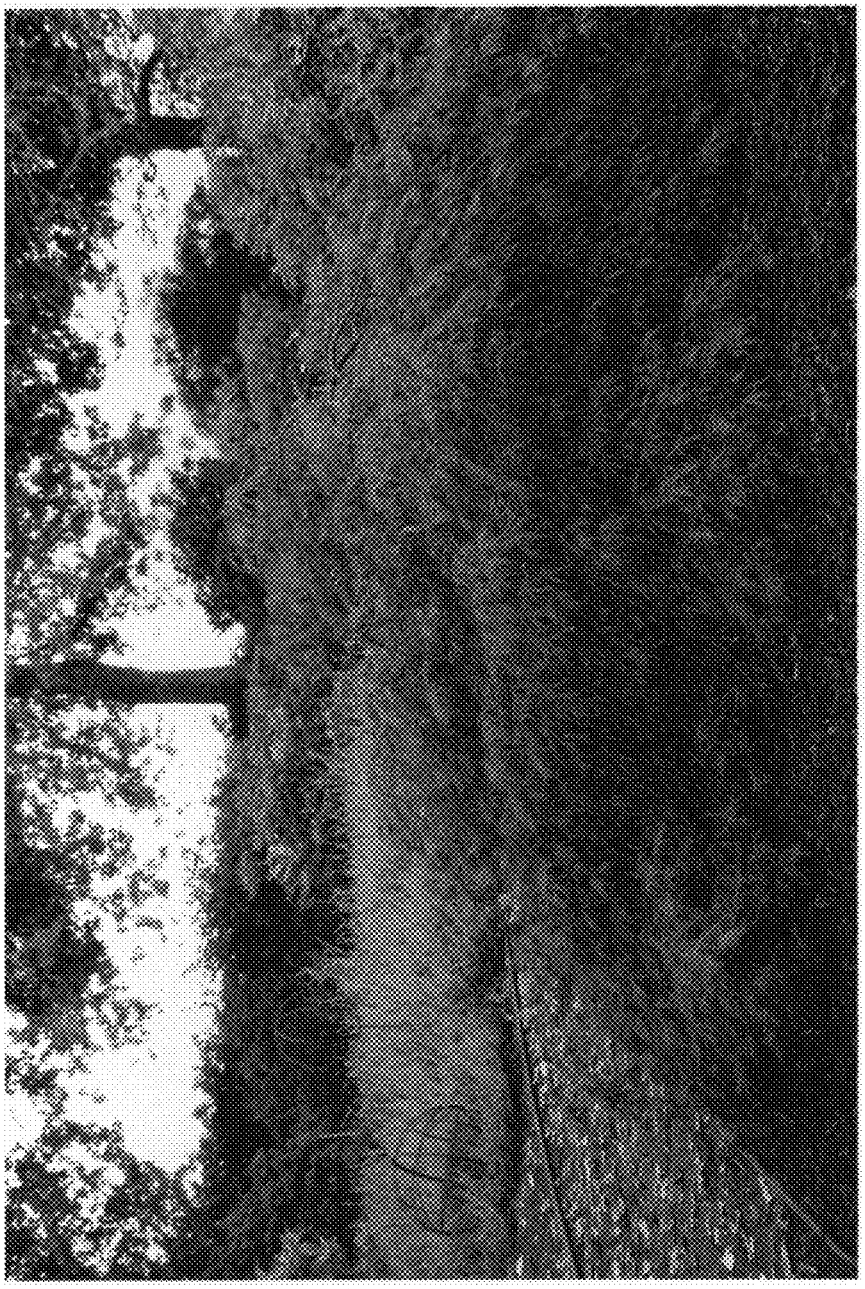
FIG. 3 is a mature tree of approximately 6 years, planted in the ground, photographed in late Summer.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MONFRICK' plants grown outdoors and in a nursery in Dayton, Oreg. Plants are approximately 2 to 3 years old, in a 5 gallon nursery container. Temperatures ranged from −8° C. to 20° C. at night to 5° C. to 35° C. during the day. Measurements and numerical values represent averages of typical plant types.

Botanical classification: *Acer palmatum* var. *dissectum* 'MONFRICK'.

PROPAGATION

Time to initiate roots: About 50 to 60 days at approximately 25° C.

Root description: Fibrous. Fine, brown roots not accurately measured with an R.H.S. chart.

PLANT

Growth habit: Weeping, deciduous dwarf tree.

Pot size of described plant: 5 gallon.

Height: 70 to 90 cm.

Plant spread: 30 to 50 cm.

Growth rate: Moderate, slowing with maturity, about 20 to 30 cm per year the first 2-3 years, then about 10 cm per year.

Branch internode length: 4 to 6 cm.

Branch characteristics:

*Length*.—Main branches are 15 to 25 cm.

*Diameter*.—5 to 15 mm.

*Texture*.—Smooth with lenticels.

*Color*.—Near RHS Greyed-Green 197D, new foliage flushed Greyed-Purple 183B on upper surface, lower surface of new growth colored Yellow-Green 144A.

Aspect and angle: Branches weeping, arching downward.

Trunk characteristics:

*Diameter*.—2.5 to 3.0 cm approximately 5 cm above soil level.

*Color*.—Near RHS Greyed-Green 197D, striated of Greyed-Purple N186B.

Other branch and trunk characteristics:

*Lenticels present*.—Yes.

*Lenticel length*.—3 to 6 mm.

*Lenticel diameter*.—2 mm.

*Lenticel density*.—Moderate.

*Lenticel color*.—Near RHS White 155C.

*Bark surface texture*.—Nearly smooth, striated.

FOLIAGE

Leaf:

*Arrangement*.—Opposite, rarely sub-opposite.

*Average length*.—Approximately 7.5 cm including petiole.

*Average width*.—Approximately 7.5 cm.

*Shape of blade*.—Overall shape broad orbicular. Cut leaf maple type with 7 lobes. Lobe depth average 6.0 cm.

*Apex*.—Acuminate.

*Base*.—Obcordate.

*Margin*.—Doubly serrate.

*Texture of top surface*.—Smooth with prominent veins.

*Texture of lower surface*.—Smooth with prominent veins.

*Leaf internode length*.—Average range 1.0 to 2.0 cm.

*Typical leaf emergence day*.—Early March in Oregon.

*Color*.—Young foliage: Upper side: Near RHS Greyed-Red 180A, lightly flushed Red 45D at base. Under side: Near RHS Greyed-Red 180C, lightly flushed Red 45D at base. Mature foliage: Upper side: Near RHS Greyed-Green 191B, heavily flushed Greyed-Purple 183B and Greyed-Red 178A. Under side: Near RHS Greyed-Green 191B, heavily flushed Greyed-Purple 183B. Mature Fall foliage: Upper side: Near RHS Greyed-Red 178A. Mid-vein Red 44B. Under side: Near RHS Greyed-Red 178A. Mid-vein Red 44C.

Foliage:

*Venation*.—Type: Palmate. Color: Venation color upper side: Near RHS Greyed-Purple N187B. Venation color under side: Near RHS Greyed-Green N189B. Petiole: Length: Average 2.0 cm. Diameter: Average 0.1 cm. Color: Upper side: Near RHS Greyed-Red 182B. Under side: Near RHS Greyed-Red 182B.

FLOWER

Flowering not observed to date.

OTHER CHARACTERISTICS

Disease/pest resistance: Neither resistance nor susceptibility to normal diseases and pests of *Acer* has been observed.

Drought resistance: No tolerance for drought.

Temperature tolerance: USDA Zones 4 through 8.

What is claimed is:

1. A new and distinct cultivar of *Acer palmatum* var. *dissectum* tree named 'MONFRICK' as herein illustrated and described.

* * * * *